(12) United States Patent
Evans (10) Patent No.: US 8,753,124 B2
(45) Date of Patent: Jun. 17, 2014

(54) METHOD AND APPARATUS FOR PRESCRIBING AND PREPARING A REPRODUCIBLE AND CUSTOMIZED DYSPHAGIA DIET

(76) Inventor: Cheryl Lynn Evans, Naperville, IL (US)

( * ) Notice: Subject to any disclaimer, the term of this patent is extended or adjusted under 35 U.S.C. 154(b) by 753 days.

(21) Appl. No.: 12/705,971

(22) Filed: Feb. 15, 2010

(65) Prior Publication Data

US 2010/0209893 A1 Aug. 19, 2010

Related U.S. Application Data

(60) Provisional application No. 61/152,726, filed on Feb. 15, 2009.

(51) Int. Cl.
*G09B 19/00* (2006.01)

(52) U.S. Cl.
USPC .......................................................... 434/127

(58) Field of Classification Search
USPC .......................................................... 434/127
See application file for complete search history.

(56) References Cited

U.S. PATENT DOCUMENTS

| | | | |
|---|---|---|---|
| 3,558,898 A | 1/1971 | Block | |
| 3,803,903 A | 4/1974 | Lin | |
| 3,875,791 A | 4/1975 | Fitzgerald | |
| 4,299,119 A | 11/1981 | Fitzgerald | |
| 4,484,468 A | 11/1984 | Gau | |
| 4,993,365 A | 2/1991 | Weestra | |
| 5,503,003 A | 4/1996 | Brookfield | |
| 5,932,235 A | 8/1999 | Ninomiya | |
| 5,976,084 A * | 11/1999 | Tymchuck | 600/300 |
| 6,145,373 A | 11/2000 | Tymchuck | |
| 6,461,589 B2 * | 10/2002 | Robbins | 424/9.41 |
| 6,568,397 B1 * | 5/2003 | Addington et al. | 128/897 |
| 6,592,863 B2 | 7/2003 | Fuchs | |
| 6,683,679 B2 | 1/2004 | Belenkii | |
| 6,887,850 B2 | 5/2005 | Fuchs | |
| 7,238,357 B2 * | 7/2007 | Barron | 424/239.1 |
| 7,593,952 B2 * | 9/2009 | Soll et al. | 1/1 |
| 7,638,150 B2 | 12/2009 | Holahan | |
| 8,481,000 B2 * | 7/2013 | Holahan | 424/1.11 |
| 2002/0044957 A1 | 4/2002 | Fuchs | |
| 2003/0044351 A1 | 3/2003 | Robbins | |
| 2004/0197459 A1 * | 10/2004 | Gaonkar et al. | 426/601 |
| 2004/0258823 A1 * | 12/2004 | Dufresne et al. | 426/573 |
| 2007/0224126 A1 * | 9/2007 | Dufresne et al. | 424/9.2 |
| 2009/0162515 A1 * | 6/2009 | Dufresne et al. | 426/573 |
| 2011/0190192 A1 * | 8/2011 | Wahren | 514/1.1 |
| 2012/0046641 A1 * | 2/2012 | Jedwab et al. | 604/503 |

FOREIGN PATENT DOCUMENTS

CA WO 2005/117617 A1 12/2005

OTHER PUBLICATIONS

Hembree et al: "Dysphagia evaluation and treatment" Operative Techniques in Otolaryngology-Head and Neck Surgery, W.B. Saunders, vol. 8, No. 4, Dec. 1, 1997.*
National Dysphagia Diet: Standardization for Optimal Care, American Dietetic Association, 2002.

(Continued)

*Primary Examiner* — Kurt Fernstrom
*Assistant Examiner* — Dolores Collins
(74) *Attorney, Agent, or Firm* — Chicago IP Law; Steven M. Evans (57) ABSTRACT

A method and apparatus for determining and prescribing a quantifiable, reproducible, and customized diet for a patient suffering from dysphagia.

19 Claims, 4 Drawing Sheets

(56) References Cited

OTHER PUBLICATIONS

Development of an objective method for assessing viscosity of formulated foods and beverages for the dysphagic diet, Linda Mann, PDt., and Kwan Wong, PhD, Jounal of the American Dietetic Association, Jun. 1996, pp. 585-588.

Grant by EPSRC, Entitled "A Self-Sensing Instrument for Investigation of Rheology in Dysphagia," Dr. BM Hanson, principal investigator, University College London (Exact publication date unknown).

Balmforth et al., "Viscoplastic dam breaks and the Bostwick consistometer," Journal of Non-Newtonian Fluid Mechanics 142 (2007) 63-78.

Perona, Paolo, "Bostwick Degree and Rheological Properties: An Up-to-Date Viewpoint," Applied Rheology 15 (2005) 218-229.

Kim, Yoen Kim, thesis as part of requirement for degree of Master of Art, entitled "Inconsistency in the Line Spread Test as an Objective Measurement of Thickened Liquids," Whichita State University, 2007.

Cichero et al., "Which One of These Is Not Like the Others? An Inter-Hospital Study of the Viscosity of Thickened Fluids," Journal of Speech, Language, and Hearing Research, vol. 43, Apr. 2000, pp. 537-547.

Bostwick Consistometer, Arrow Scientific, advertisement on web page http://www.arrowscientific.com.au/bostwick_consistometer.html (original publication date unknown).

Paik NJ et al., Arch Phys Med Rehabil, "Categorization of dysphagia diets with line spread test;" Department of Rehabilitation Medicine, Seoul National University College of Medicine, Seoul, Republic of Korea (May 2004).

"DDP Guidelines," a dysphagia diet sold by Vocatek, Inc., copyright 1999, 2002, 2006.

Phagia Hand Held Viscometer, sold by Med-Diet Laboratories, 3600 Holly Lane, Suite 80, Plymouth, MN 55447. Publication date of advertisement brochure unknown.

\* cited by examiner

METHOD AND APPARATUS FOR PRESCRIBING AND PREPARING A REPRODUCIBLE AND CUSTOMIZED DYSPHAGIA DIET

CROSS-REFERENCE TO RELATED APPLICATION

This non-provisional patent application claims priority and benefit of U.S. provisional patent application having application No. 61/152,726, filed on Feb. 15, 2009, and entitled "METHOD AND APPARATUS FOR QUANTIFYING DYSPHAGIA FOODS FOR PATIENT CONSUMPTION," the content of which is hereby incorporated by reference in its entirety.

FIELD OF THE INVENTION

The present invention relates generally to preparing food diets for patients having difficulty swallowing. More particularly, the present invention relates to a method and an apparatus to facilitate preparing more accurate food diets for dysphagia patients.

BACKGROUND OF THE INVENTION

Dysphagia is a swallowing disorder, wherein a person is unable to swallow or has difficulty swallowing. Dysphagia often runs concurrent to many acquired and chronic medical conditions and is known to affect both adults and children. Some of these medical conditions include stroke, Parkinson disease, cerebral palsy, or respiratory disorders. Left untreated, dysphagia can cause health complications such as aspiration, malnutrition, dehydration, asphyxia, recurrent respiratory infections and death.

Dysphagia is diagnosed by clinical professionals, typically speech-language pathologists, who are educated in anatomy and physiology of the oral and pharyngeal mechanisms responsible for deglutition. Diagnosis of dysphagia is typically determined through a clinical evaluation which may or may not include use of technology such as a videofluroscopic swallow study (VFSS). A VFSS is generally conducted in a radiology suite by a speech-language pathologist in conjunction with a radiologist. The purpose of the swallowing evaluation is to determine if there is dysfunction in the swallowing mechanism and the type and severity of the dysfunction. Once the diagnosis of dysphagia is made and the type and severity is determined, treatment to remediate and/or compensate for the disorder is initiated.

Medical professionals generally treat dysphagia patients by modifying the consistency of foods and liquids consumed by dysphagia patients. Diet modification typically is the most common used compensatory strategy to manage dysphagia patients. Foods are routinely altered by adding a commercial thickener, and foods are generally thinned by adding water or other thin liquid. Some examples of commercial thickeners include cornstarch and baby cereal. Currently, foods for dysphagia patients are generally thinned or thickened to fall within one of a group of pre-established diet-type categories to quantify the thickness of the liquids, such as honey thickness, nectar thickness and thin liquids. The exact characteristics for each of these or other pre-established dysphagia diets are undefined and not standardized. Dysphagia patients are typically placed within one of these diet categories, even though that particular diet category may not precisely meet the needs of that patient.

Moreover, the current process for determining the thickness of liquids and foods for each of the dysphagia diet categories is based on individual judgment. The conventional method is problematic due to the inherent inconsistencies and ambiguousness of the dysphagia diets. A dysphagia diet typically requires all liquids and foods eaten by the patient to be altered in consistency by blending and/or thickening. In such a procedure, there is no set, uniform measurement to determine the thickness or consistency of the liquids and foods prescribed to the dysphagia patient. Presently, therapists typically pour foods or liquids into a container, add water or a commercial thickener, and stir the mixture until the mixture appears to be the proper consistency. More water or thickener is added until the therapist visually estimates whether the consistency is appropriate, using their best clinical guess.

A therapist may also pour the mixture from a spoon to visually determine the consistency. The mixture is then classified into one of predetermined groups, such as (1) "honey" thickness, (2) "nectar" thickness or (3) "thin," depending on what consistency it most resembles. If a dysphagia diet is prescribed and a liquid consistency is deemed appropriate for the patient, the patient is instructed to drink only one of the predetermined classifications of consistency prescribed, and no other consistency, because other consistencies could be aspirated (take liquids into their lungs). Aspiration can have serious and deadly consequences to a patient's health, such as causing pneumonia, weight loss, fevers, recurrent respiratory illness, or even death. Unfortunately, without a consistent, standardized measurement system, the perception of "honey," "nectar" and "thin" liquids is so variable between people that they are rarely the same. Even the same therapist can mix two separate batches of liquids and foods and have resulting variations in the consistency. For a patient, such variations can be deadly.

Further adding to the problem, dysphagia patients are routinely transferred between medical facilities in clinical care. As a dysphagia patent's condition improves, the dysphagic patient may often move from acute care to subacute care, then to a rehabilitation facility, then to a long-term care facility, and then perhaps to their home. The potential for problems, in terms of quality of care that the patient receives, increases with each transfer between treatment locations because of variability between caregivers in the preparation of food consistencies. A specific technical problem is the inability for a patient or their caregiver to replicate the food consistency with that patient's prescribed dysphagia diet.

Current and common methods of treatment include: 1) providing patients with written descriptive diet plans containing examples of recommended foods and liquids, or 2) recommending purchase of a particular commercially prepared product based on its viscosity. Neither of these current treatment methods is optimal. Written descriptive diets require the preparer of the dysphagia diet food and/or liquids to estimate the appropriate consistency or viscosity by visually comparing it to another similar food item.

On the other hand, manufacturers use different techniques and machinery which are not consistent with each others manufacturing methods. Consequently, manufacturers of dysphagia food products have different standards of consistency and viscosity. Therefore, the patient may inadvertently consume an inappropriate consistency if they use products from different manufacturers, placing themselves at risk for aspiration or other health consequences.

While the exact number of people suffering from dysphagia is unknown, the occurrence of dysphagia in older people is significant, especially people who have suffered an acute, first-time stroke. The U.S. Census Bureau estimates that 16,500,000 people will require care for dysphagia by the year 2010.

Viscometers are available for commercial and clinical use, but these devices are not designed for a patient and/or caregiver to use independently at home. Presently, there is no technique, procedure or method for clinical professionals, caregivers or patients to independently determine acceptable prescribed foods and liquids based on objective determinations.

Accordingly, there is a strong need for a quantitative measurement system that can easily measure food characteristics for dysphagia patients, enabling foods to be reproduced having consistent properties, regardless of the manufacturer, cook, or therapist preparing the food. There also is a need for customized dysphagia diets that more precisely meet the specific needs of each dysphagia patient.

OBJECTS AND SUMMARY OF THE INVENTION

In view of the forgoing, an object of the present invention is to provide a method for quantifying a customized dysphagia food diet for a patient, instead of forcing the patient into one of a group of predetermined dysphagia diets that may not be suitable for the specific needs of that dysphagia patient.

Another object of the present invention is to provide a method for more accurately defining the type and severity of a patient's particular dysphagia.

A further object of the present invention is to provide a method for prescribing a customized dysphagia diet that fits the specific needs of a dysphagia patient, instead of placing the patient into one of a group of "one-size-fits-all" predetermined dysphagia diets.

An additional object of the present invention is to provide an apparatus enabling a medical professional to more accurately define the type and severity of a patent's dysphagia.

In that regard, a further object of the present invention is to provide an apparatus to enable a medical professional to prescribe a dysphagia diet that is customized to more accurately address the specific type and severity of a patient's dysphagia.

Another object of the present invention is to provide an apparatus that enables a treating speech therapist, caregiver, or patient to prepare or reproduce foods that are more accurately consistent with the prescribed dysphagia diet for a particular patient.

Furthermore, an object of the present invention is to provide an inexpensive and durable apparatus that accurately measures a quantifiable characteristic of liquid foods that enables the diagnosing professional to prescribe a customized dysphagia diet that addresses the needs for the specific type and severity of a patient's dysphagia, and then even further, enables the treating professional, caregiver, or the patient to accurately reproduce foods consistent with the parameters of the prescribed customized dysphagia diet for that particular patient.

Additional objects of the present invention include (1) enabling patients to eliminate the cost of expensive prepackaged, commercially prepared food and liquid products, (2) enabling patients to make safe food and liquid choices, (3) enabling patients to stay within the confines of the prescribed quantified food characteristic range, (4) allowing patients to prepare foods and drinks at home that are more preferable to their specific taste and/or ethnic background, and (5) eliminating health risks associated with consumption of inappropriate consistencies caused by using products from different manufacturers. It should be noted that the word "food" in this application refers to solid foods and liquid foods.

In order to achieve the objects set forth above, the present invention provides a method including the steps of: performing a swallowing evaluation upon a patient to determine whether the patient suffers from dysphagia; selecting a quantifiable food characteristic that can be objectively measured; preparing multiple foods having different values of unit measure for a quantifiable food characteristic; using a first apparatus for measuring the quantifiable food characteristic of each of the multiple prepared foods; administering to the patient each of the multiple prepared foods having different values for the quantifiable food characteristic; observing the patient's ability to swallow each of the multiple foods having a different value for the quantifiable food characteristic; determining a safe range of values for the quantifiable food characteristic based on the patients ability to swallow each of the multiple foods; prescribing a customized dysphagia diet comprising the safe range of values for the quantifiable food characteristic for designating foods acceptable for consumption by the dysphagia patient; preparing food for consumption for the patient pursuant to the customized dysphagia diet, wherein the quantifiable food characteristic of the prepared food falls within the range of unit measure of the prescribed customized dysphagia diet; and using a second apparatus, having a similar design to the first apparatus, for measuring the quantifiable food characteristic of the food prepared for consumption by the patient pursuant to the customized dysphagia diet.

The present invention provides an apparatus comprising a chute having a first and second end, where the first end is closed; a gate in the chute located proximate the first end and forming a retention area between the gate and the closed end of the chute; a first liquid sensor located proximate outside the gate on the bottom of the chute; a second liquid sensor proximate the second end of the chute; a timer electrically connected to the first and second liquid sensors for receiving signals from the first and second liquid sensors for calculating the period of time for a liquid to flow between the first and second liquid sensors; and a display electrically connected to the timer for displaying elapsed time for a liquid to flow in the chute between the first and second liquid sensors.

Other features and advantages of the present invention will become apparent to those skilled in the art from the following detailed description. It should be understood that the detailed description and specific examples, while indicating the preferred embodiment of the present invention, are given by way of illustration and not limitation. Many changes and modifications within the scope of the present invention may be made without departing from the spirit of the invention, and the invention includes all such modifications.

DETAILED DESCRIPTION OF THE PREFERRED EMBODIMENTS

Figure 1:
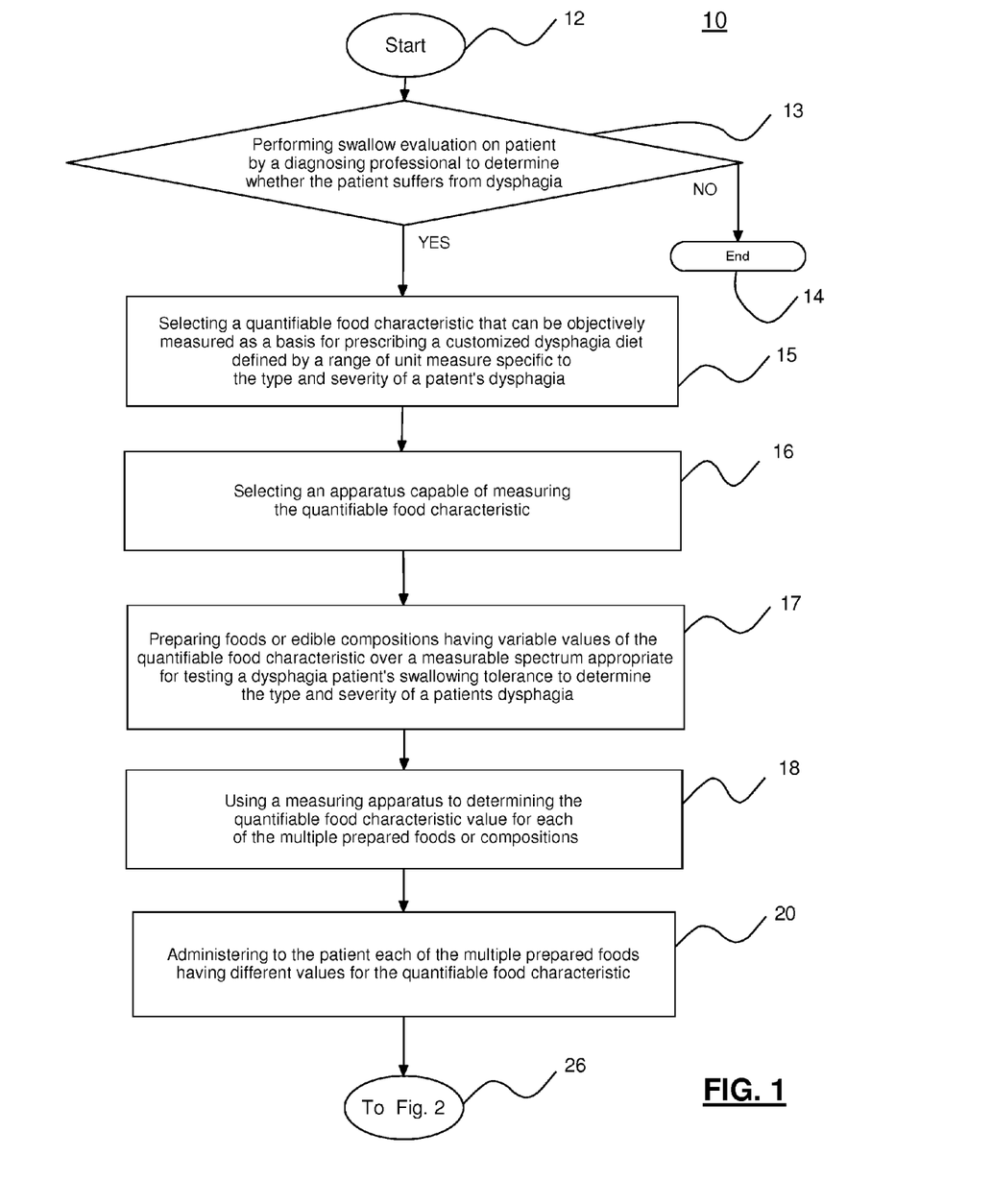
FIG. 1 is a flowchart of a preferred method of the present invention.
Figure 2:
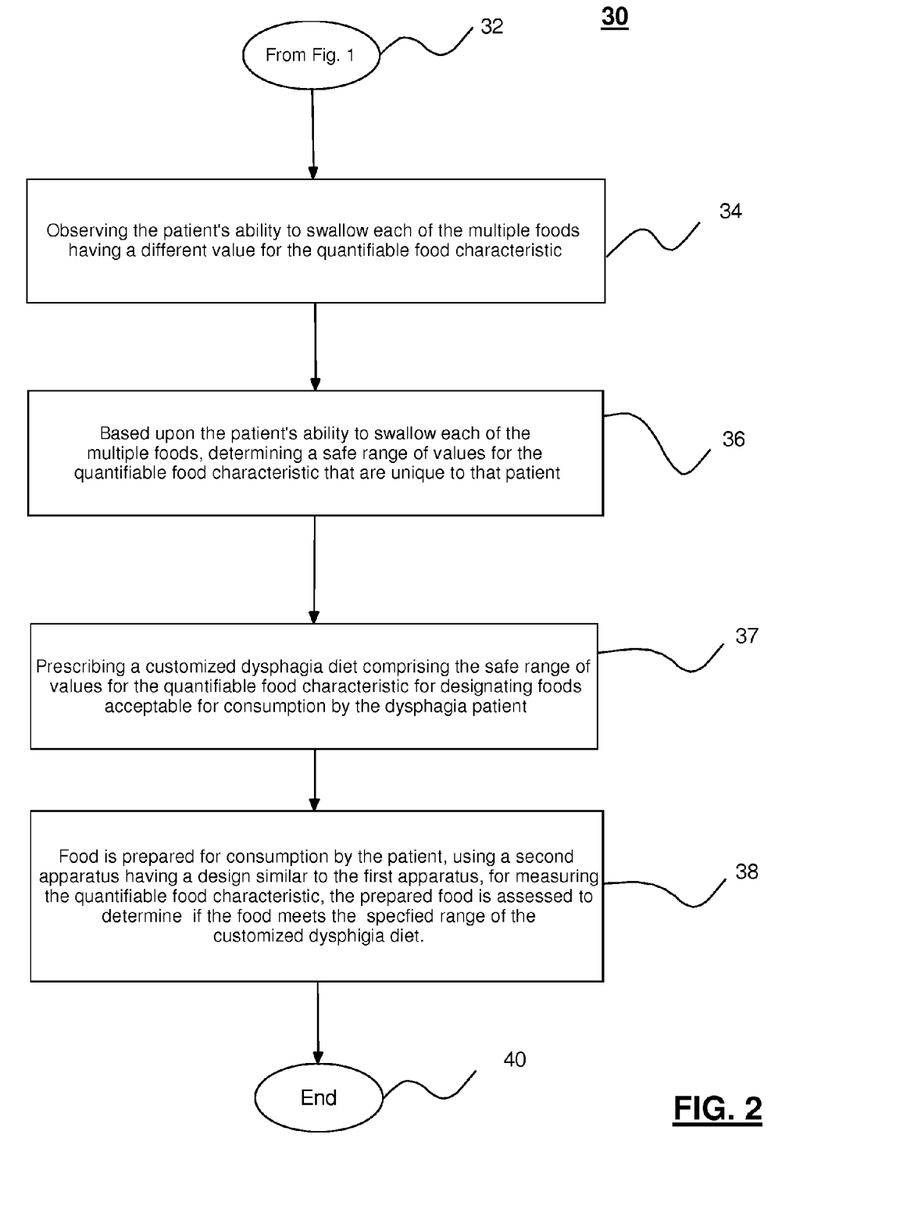
FIG. 2 is a continuation of the flowchart shown in FIG. 1.

Referring now to the drawings, FIGS. 1 and 2 are a flowchart of the preferred method of the present invention. The flowcharts 10 and 30 illustrate the steps for evaluating and diagnosing the type and severity of a patient suffering from dysphagia. The flowcharts 10 and 30 further illustrate a process for prescribing a customized dysphagia diet for a patient and a process for reproducing foods consistent with the customized dysphagia diet.

Beginning at the start 12, a patient is first evaluated at step 13 to determine if the patient is suffering from dysphagia. If the test is negative, the process terminates at step 14. If the swallowing evaluation at step 13 indicates the patient is suffering from dysphagia, the process moves to step 15.

In accordance with the present invention at step 15, a quantifiable food characteristic is selected that can be objectively measured as a basis for prescribing a customized dysphagia diet defined by a range of unit measure specific to the type and severity of a patient's dysphagia. For example, a quantifiable food characteristic could be flow rate or viscosity.

Next is step 16 an apparatus is selected for measuring the selected quantifiable food characteristic. For example, a Bostwick consistometer, a viscometer, or the line spread test could be used to measure flow rate. All of these measuring apparatuses or techniques are well known to speech pathologists, who are skilled in the art of diagnosing and treating dysphagia. Preferably, the quantifiable food characteristic, such as flow rate, could preferably be measured using one of the novel measuring apparatuses set forth in this application.

Next at step 17 foods or edible compositions (such as a barium mixture used in a videofluroscopic swallow study (VFSS)) are prepared having variable values of the quantifiable food characteristic over a measurable spectrum appropriate for testing a dysphagia patient's swallowing tolerance to determine the type and severity of a patient's dysphagia.

At step 18 the selected apparatus is used to determine the quantifiable food characteristic value for each of the multiple prepared foods or compositions. Next at step 20, the diagnosing professional administers to the patient each of the multiple prepared foods having different values for the quantifiable food characteristic.

FIG. 2 illustrates the next step 34, wherein the diagnosing professional or speech pathologist observes the patient's ability to swallow each of the multiple foods having a different value for the quantifiable food characteristic.

Based upon the patient's ability to swallow each of the multiple foods, at step 36 the diagnosing professional determines a safe range of values for the quantifiable food characteristic that are unique or customized for the patient to more accurately and precisely define and foods acceptable for consumption by the patient.

At step 37 the diagnosing professional prescribes a customized dysphagia diet comprising the safe range of values for the quantifiable food characteristic for designating foods acceptable for consumption of the dysphagia patient.

As step 38 foods are prepared for consumption by the patient, using a second apparatus having a similar design to the first apparatus that measured the quantifiable food characteristic that enabled the diagnosing professional to prescribe a customized diet for the patient. By using an apparatus similar to the apparatus used in measuring the quantifiable foods for diagnosing the patient, the patient can easily and accurately reproduce foods that are consistent with the patient prescribed dysphagia diet.

Figure 3:
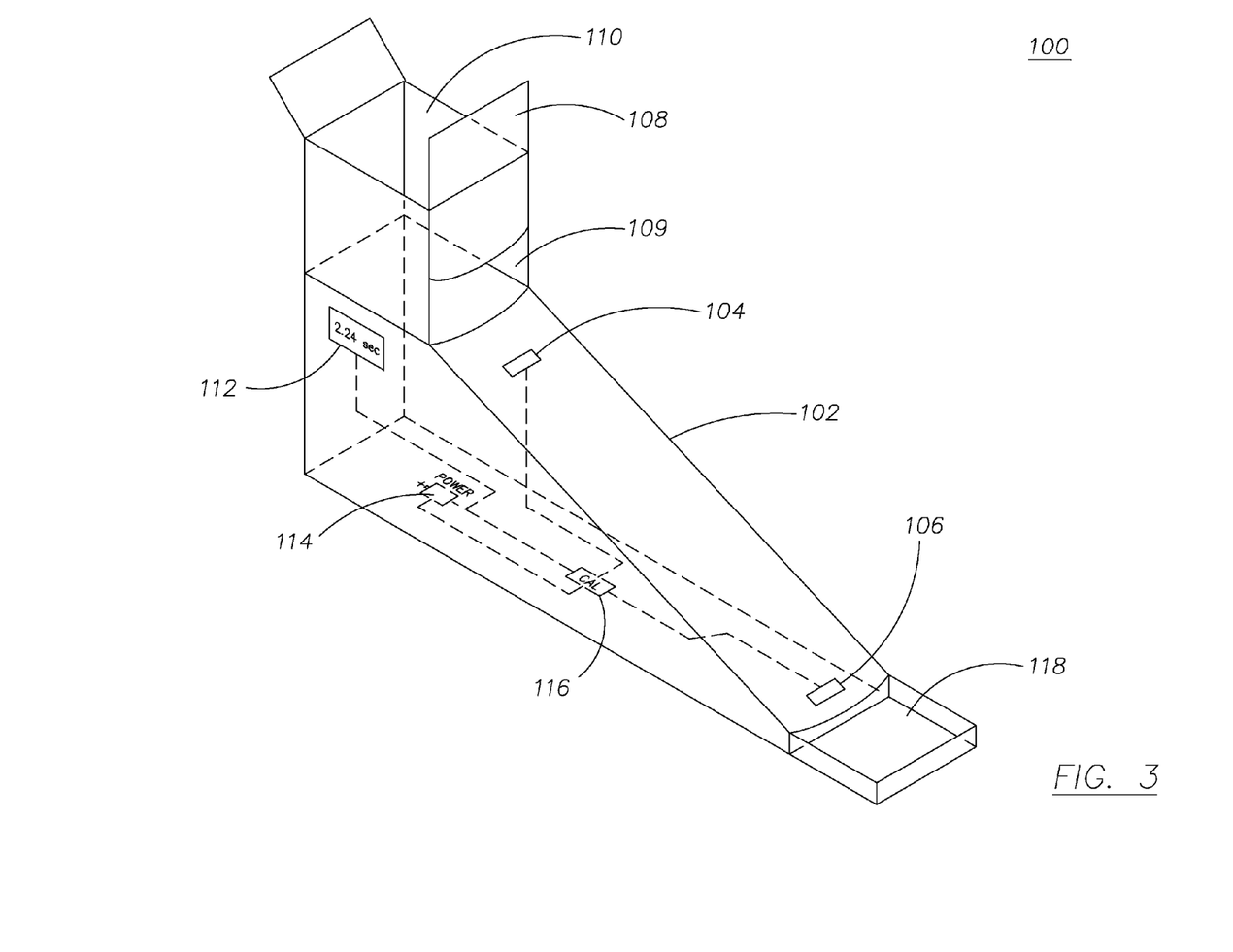
FIG. 3 is a perspective view of an apparatus constructed in accordance with the present invention.

FIG. 3 illustrates a perspective view of an apparatus configured in accordance with the present invention. The flow meter 100 is configured in accordance with the present invention. The flow meter has a ramp or chute 102 that includes a first liquid sensor 104 and a second liquid sensor 106. The liquid sensors 104, 106 are located in the lower floor or curved section of the chute 102. Preferably, the liquid sensors 104, 106 are covered with a glass covering in an aperture in the chute 102, enabling the liquid sensors 104,106 to optically detect liquid as it flows over the sensors 104 and then 106. The liquid sensors can be of a type disclosed in U.S. Pat. No. 3,558,898 ('898) and U.S. Pat. No. 6,683,679 ('679), which are both hereby incorporated by reference in their entirety. The '898 patent is entitled a "Flow Measurement System Using Time Correlation of Two Photocell Signals," and the '679 patent is entitled an "Optical Flow Monitor."

The upper portion of the chute 102 is connected to a reservoir or retention area 110. A gate 108 is formed into a wall of the retention area 110. The gate 108 can be slid up to create an opening 109 which allows liquid contained within the retention area to flow down the chute 102. When the gate 108 is opened, liquid in the retention area is released and flows down the chute 102 into a receiving receptacle 118. When the gate 108 is opened, liquid from the retention area will first pass over the first liquid sensor 104 and then the second liquid sensor 106. An electronic timer/calculator 116 determines the time it took for the liquid to flow between liquid sensors 104 and 106. The time is displayed upon display 112. The calculator 116 may be similar to the design disclosed in the electronic time-correlating system 28 of the '898 patent incorporated by reference. A battery 114 can be used to provide power to the timer 116 and sensors 104,106.

Figure 4:
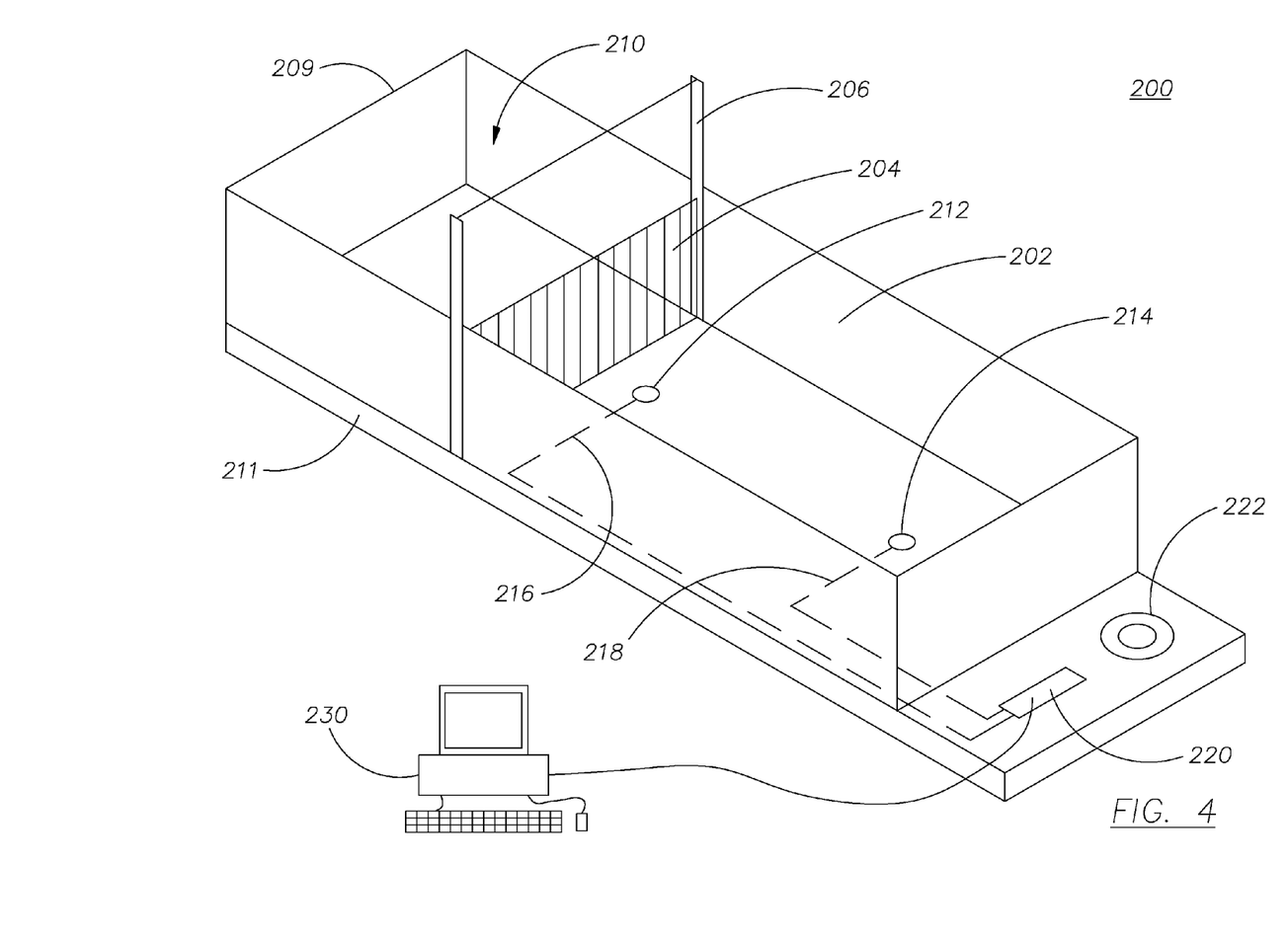
FIG. 4 is a perspective view of another apparatus constructed in accordance with the present invention.

FIG. 4 illustrated another flow meter 200 configured in accordance with the present invention. The flow meter 200 is similar to the Bostwick consistometer with some additional improvements. A chute 202 is provided that can be constructed out of plastic or metal. The chute 202 includes a first liquid sensor 212 and a second liquid sensor 214, which may be similar to the liquid sensors 104,106 discussed above. A bubble level 222 is included for leveling the chute 202. Electrical connections 216 and 218 from the liquid sensors 212 and 214, respectively, electrically connect the liquid sensors 212 and 214 to a connector 220. The connector 220 can be a USB socket or similar computer connector.

A gate 204 is located in the chute 202 near the first end 209 of the chute 202. The first end 209 of the chute 202 is closed. A retention area or reservoir 210 is formed by the gate 204 and closed end 209 of the chute 202. The gate 204 is open by sliding up along a runner 206. When the gate 204 is opened, liquid contained within the retention area 210 flows out along the chute, first over sensor liquid 212 and then liquid sensor 214, which each send detection signal to a personal computer 230 that is electrically connected to the sensors 212,214 via the connector 220. The personal computer 230 provides power to the sensors 212,214 and also performs the timing calculations to determine the time it takes for liquid to flow from the reservoir 210 and pass between liquid sensor 212 and liquid sensor 214. The computer also functions as a display for indicating the time interval for the liquid to flow between sensors 212 and 214. The computer 230 can be programmed to perform far more complicated tasks, such as managing multiple patient data and correlating flow data with different food types. A huge advantage of this design is the cost to a consumer, be it a patient or speech pathologist, of the flow meter is very inexpensive because the power and complicated electronics are contained within the personal computer, which would typically already be owned by the consumer.

It should be understood that the above description of the present invention and preferred embodiment are given by way of description and illustration, and not limitation. Many changes and modifications within the scope of the present

I claim as I my invention:

1. A method for determining and prescribing a quantifiable, reproducible and customized diet for a patient suffering from dysphagia, said method comprising the steps of:
   providing an electronic flow meter, comprising:
      an inclined chute having an upper end and a lower end;
      a first optical sensor located proximate the upper end of the chute;
      a second optical sensor located proximate the lower end of the chute;
      a timer receiving electrical signals from the first optical sensor and the second optical sensor indicating when a flowable food passes the first optical sensor and the second optical sensor, and calculating elapsed time there between; and
      a display indicating elapsed time for flowable food to flow between the first optical sensor and the second optical sensor;
   administering for consumption to a patient a flowable food having an initial quantifiable flow rate;
   determining whether the patient medically tolerates consumption of the flowable food having the initial quantifiable flow rate, thereby being able to consume said flowable food having the initial quantifiable flow rate without associated health risks of dysphagia;
   administering for consumption to the patient, who has medically tolerated the flowable food having the initial quantifiable flow rate, additional flowable food having increasing quantifiable flow rates until the patient is unable to medically tolerate without associated health risks of dysphagia flowable food having a further increase in quantifiable flow rate;
   measuring flow rate at room temperature using the electronic flow meter of the flowable food having highest quantifiable flow rate tolerated without associated health risks of dysphagia by the patient, which is designated as a first quantifiable end of a customized quantifiable dysphagia diet range;
   administering for consumption to the patient, who has medically tolerated the flowable food having the initial flow rate, additional flowable foods having decreasing quantifiable flow rates until the patient is unable to medically tolerate without associated health risks of dysphagia a further decrease in flow rate of flowable food;
   measuring flow rate at room temperature using the electronic flow meter of flowable food having lowest quantifiable flow rate tolerated without associated health risks of dysphagia by the patient, which is designated as a second quantifiable end of the customized quantifiable dysphagia diet range; and
   prescribing a customized quantifiable dysphagia diet range to the patient consisting of foods having flow rates between the first quantifiable end and the second quantifiable end of the customized quantifiable dysphagia diet range, thereby enabling the patient to reproduce flowable foods having quantifiable flow rates within the prescribed customized quantifiable dysphagia diet range.

2. The method of claim 1, further comprising the step of:
   using the electronic flow meter by the patient for measuring the flow rate to determine acceptable foods for consumption in accordance with the prescribed customized dysphagia diet.

3. The method of claim 1, wherein the determining steps include performing a Videofluroscopic Swallow Study (VFSS).

4. The method of claim 1, wherein the determining steps include performing a Modified Barium Swallow (MBS) study.

5. The method of claim 1, wherein the determining steps include a Fiberendoscopic Examination of Swallow (FEES) study.

6. The method of claim 1, wherein the determining steps include a clinical swallow exam.

7. The method of claim 1, wherein the determining steps include a bedside swallow exam.

8. The method of claim 1, wherein the step of determining whether a patient medically tolerates consumption of the flowable food includes at least one of coughing, choking, wet vocal quality, pocketing of foods in cheeks of mouth, excessive chewing of food, drooling, aspiration, and food sticking in throat.

9. The method of claim 1, wherein the flowable food comprises at least one of liquid, pureed food, and barium.

10. The method of claim 1, wherein the chute is exposed to ambient environment.

11. The method of claim 1, wherein the chute is inclined at a predetermined angle.

12. The method of claim 1, wherein the electronic flow meter further comprises a data port for a computer.

13. The method of claim 1, where the timer and the display are part of a computer.

14. A method for determining and prescribing a quantifiable, reproducible, and customized diet for a patient suffering from dysphagia, said method comprising the steps of:
   utilizing an electronic flow meter, comprising:
      an inclined chute having an upper end and a lower end;
      a first optical sensor located proximate the upper end of the chute;
      a second optical sensor located proximate the lower end of the chute;
      a timer receiving electrical signals from the first optical sensor and the second optical sensor indicating when a flowable food passes the first optical sensor and the second optical sensor, and calculating elapsed time there between; and
      a display indicating elapsed time for flowable food to flow between the first optical sensor and the second optical sensor;
   administering for consumption to a patient a flowable food having an initial quantifiable flow rate;
   determining whether the patient medically tolerates consumption of the flowable food having the initial quantifiable flow rate, thereby being able to consume said flowable food having the initial quantifiable flow rate without associated health risks of dysphagia;
   administering for consumption to the patient, who has medically tolerated the flowable food having the initial quantifiable flow rate, additional flowable food having increasing quantifiable flow rates until at least one of (i) the patient is unable to medically tolerate without associated health risks of dysphagia flowable food having a further increase in quantifiable flow rate and (ii) administered food has a flow rate of water;
   measuring flow rate at room temperature using the electronic flow meter of the flowable food having highest quantifiable flow rate tolerated without associated health risks of dysphagia by the patient, which is designated as a first quantifiable end of a customized quantifiable dysphagia diet range;

administering for consumption to the patient, who has medically tolerated the flowable food having the initial flow rate, additional flowable foods having decreasing quantifiable flow rates until one of (i) the patient is unable to medically tolerate without associated health risks of dysphagia a further decrease in flow rate of flowable food and (ii) administered food has a predetermined minimum flow rate;

measuring flow rate at room temperature using the electronic flow meter of flowable food having lowest quantifiable flow rate tolerated without associated health risks of dysphagia by the patient, which is designated as a second quantifiable end of the customized quantifiable dysphagia diet range; and prescribing a customized quantifiable dysphagia diet range to the patient consisting of foods having flow rates between the first quantifiable end and the second quantifiable end of the customized quantifiable dysphagia diet range, thereby enabling the patient to reproduce flowable foods having quantifiable flow rates within the prescribed customized quantifiable dysphagia diet range.

15. The method of claim 14, wherein the electronic flow meter further comprises a data port for a computer.

16. The method of claim 14, where the timer and the display are part of a computer.

17. A method for determining and prescribing a quantifiable, reproducible, and customized diet for a patient suffering from dysphagia, said method comprising the steps of:

utilizing an electronic flow meter, comprising:
- a chute having a first closed end and a second opposing end;
- a gate proximate the closed end, wherein a retention area is formed between the closed end and the gate;
- a first optical sensor located proximate and on side of gate opposite the retention area;
- a second optical sensor located proximate the second end of the chute;
- a timer receiving electrical signals from the first optical sensor and the second optical sensor indicating when a flowable food passes the first optical sensor and the second optical sensor, and calculating elapsed time there between; and
- a display indicating elapsed time for flowable food to flow between the first optical sensor and the second optical sensor;

administering for consumption to a patient a flowable food having an initial quantifiable flow rate;

determining whether the patient medically tolerates consumption of the flowable food having the initial quantifiable flow rate, thereby being able to consume said flowable food having the initial quantifiable flow rate without associated health risks of dysphagia;

administering for consumption to the patient, who has medically tolerated the flowable food having the initial quantifiable flow rate, additional flowable food having increasing quantifiable flow rates until at least one of (i) the patient is unable to medically tolerate without associated health risks of dysphagia flowable food having a further increase in quantifiable flow rate and (ii) administered food has a flow rate of water;

measuring flow rate at room temperature using the electronic flow meter of the flowable food having highest quantifiable flow rate tolerated without associated health risks of dysphagia by the patient, which is designated as a first quantifiable end of a customized quantifiable dysphagia diet range;

administering for consumption to the patient, who has medically tolerated the flowable food having the initial flow rate, additional flowable foods having decreasing quantifiable flow rates until one of (i) the patient is unable to medically tolerate without associated health risks of dysphagia a further decrease in flow rate of flowable food and (ii) administered food has a predetermined minimum flow rate;

measuring flow rate at room temperature using the electronic flow meter of flowable food having lowest quantifiable flow rate tolerated without associated health risks of dysphagia by the patient, which is designated as a second quantifiable end of the customized quantifiable dysphagia diet range; and prescribing a customized quantifiable dysphagia diet range to the patient consisting of foods having flow rates between the first quantifiable end and the second quantifiable end of the customized quantifiable dysphagia diet range, thereby enabling the patient to reproduce flowable foods having quantifiable flow rates within the prescribed customized quantifiable dysphagia diet range.

18. The method of claim 17, wherein the chute is level.

19. The method of claim 17, wherein the chute is inclined.

* * * * *